United States Patent [19]

Vargas

[11] 4,114,618
[45] Sep. 19, 1978

[54] CATHETER ASSEMBLY

[76] Inventor: Jorge J. Vargas, 9106 Bonhomme Rd., Houston, Tex. 77074

[21] Appl. No.: 750,740

[22] Filed: Dec. 15, 1976

[51] Int. Cl.² ............................................. A61M 5/00
[52] U.S. Cl. .................................. 128/214.4; 128/348
[58] Field of Search ..................... 128/214.4, 221, 348, 128/350 R, 357, DIG. 26, 133

[56] References Cited

U.S. PATENT DOCUMENTS

| 2,935,068 | 5/1960 | Donaldson | 128/348 |
| 3,225,762 | 12/1965 | Guttman | 128/214.4 |
| 3,388,703 | 6/1968 | Bowes | 128/214.4 |
| 3,430,300 | 3/1969 | Doan | 128/DIG. 26 |
| 3,506,007 | 4/1970 | Henkin | 128/214.4 X |
| 3,677,250 | 7/1972 | Thomas | 128/348 |
| 3,835,863 | 9/1974 | Goldberg et al. | 128/350 R |

FOREIGN PATENT DOCUMENTS 1,037,523   4/1953   France ................... 128/214 R Primary Examiner—Dalton L. Truluck
Attorney, Agent, or Firm—Pravel, Wilson & Gambrell

[57] ABSTRACT

A catheter assembly insertable into a blood vessel for directing medicinal fluids intravenously into the vessel while providing for substantially uninterrupted flow of blood through the vessel; and, an anchoring flap mountable onto the catheter assembly or any other catheter for anchoring such catheters in a variety of positions.

9 Claims, 8 Drawing Figures

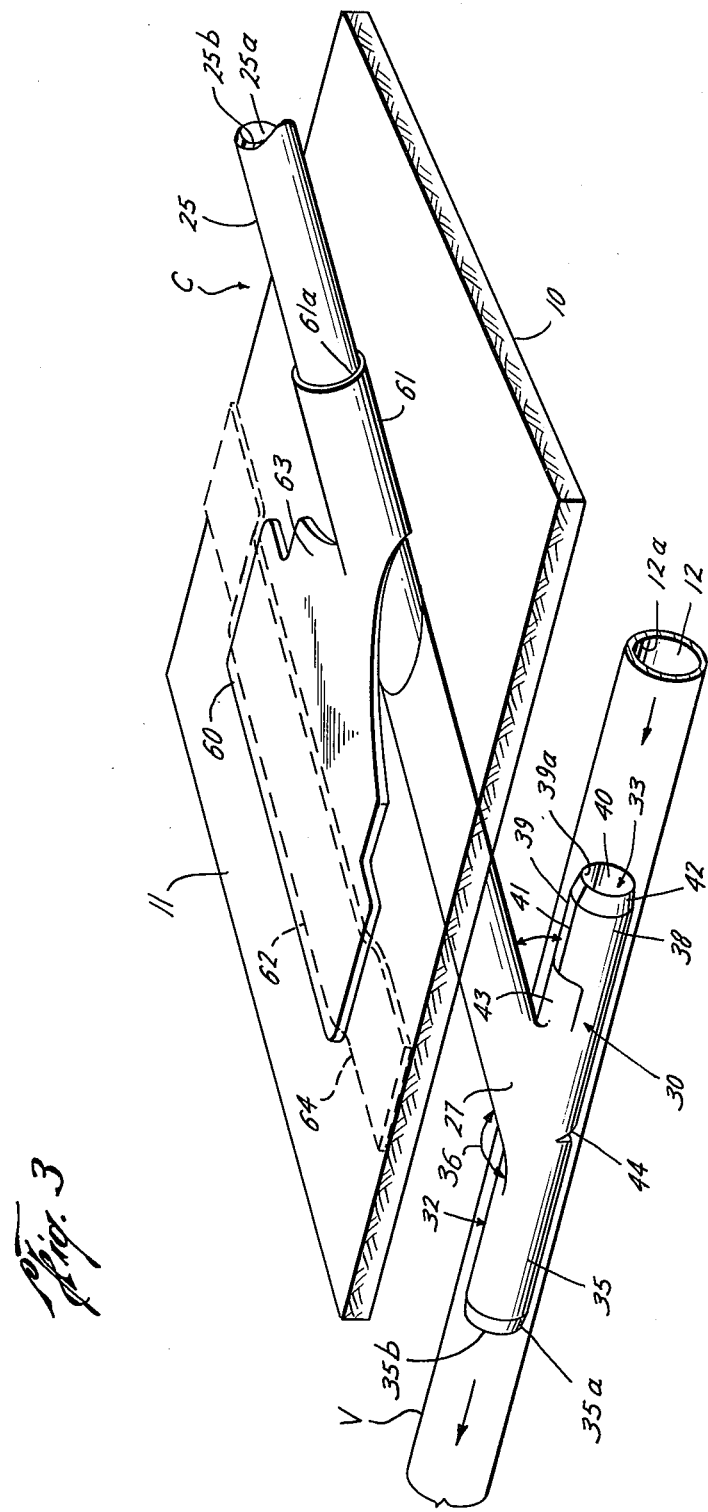

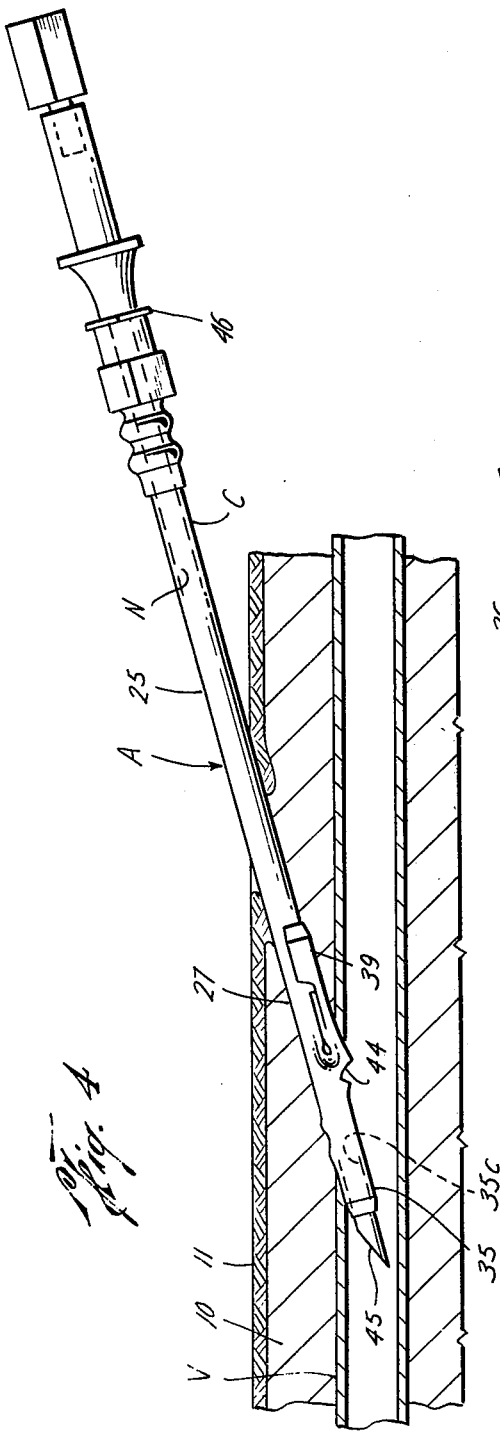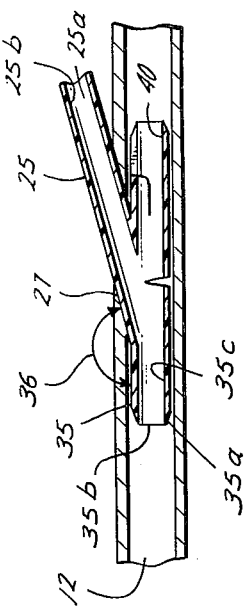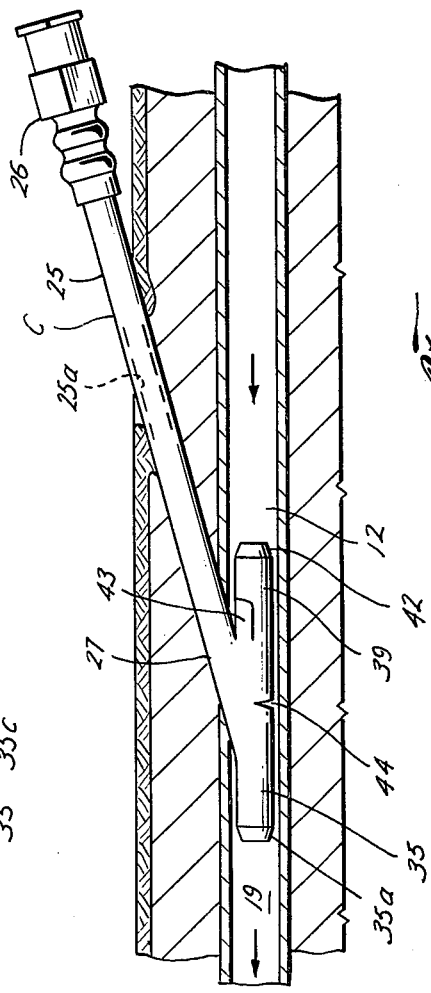

CATHETER ASSEMBLY

BACKGROUND OF THE INVENTION

The field of this invention is catheter assemblies and anchoring units therefor for use in intravenous feeding of medicinal fluids to the body.

In the field of medicine, percutaneous catheters are inserted through the skin for transferring medicinal fluid from a supply container to a blood vessel. Generally, such catheters are first inserted into a blood vessel and then connected to a supply container for the introduction of fluid by gravity flow or under positive pressure into the vessel. A well-known prior art intravenous includes a hollow, intravenous catheter portion having a tubular portion with a longitudinally extending lumen or wall portion therethrough. A hub portion is mounted onto one end of the catheter. The hub portion is adapted to be connected to a suitable transfer tube which extends to a supply container. This prior art catheter is inserted by means of a hollow needle or stylet which is initially mounted within the bore or lumen of the catheter. The sytlet terminates in a very sharp point so that the user is able to utilize the internally mounted stylet to penetrate the skin and locate the tubular portion within a blood vessel. Thereafter, the stylet is removed and the catheter hub is connected to the transfer tube connected to the supply container. Perhaps the most significant disadvantage of this type of prior art catheter results from the catheter occupying substantially the entire area of the blood vessel, thereby obstructing normal blood flow through the vessel. U.S. Pat. Nos. 3,727,613 3,225,762 and 3,776,239 are exemplary of catheter assemblies.

U.S. Pat. Nos. 3,835,863; 2,819,719; 2,790,442; and, 2,624,341 disclose drainage devices that are surgically inserted into the body and thereafter removed. Such catheters are principally used as drainage devices only and differ distinctly from the percutaneous-type catheters which must be inserted through the skin. U.S. Pat. No. 2,042,900 discloses a catheter assembly which is utilized in embalming.

Another very practical problem with catheters such as disclosed in the Guttman patent is maintaining the inserted catheter in a stable position; for catheters such as those disclosed in the Guttman patent are subject to movement or "plowing" within the blood vessel due to movement of the patient or equipment. Such movement or plowing of the catheter causes extreme irritation to the patient and may actually permanently damage either the blood vessel or the skin surrounding the catheter. Various attempts have been made to suitably anchor a catheter against such undesired movement. For example, U.S. Pat. No. 3,973,565 of Steer discloses a cannula which is fitted with laterally extending wings and a flexible sheet of material having an adhesive surface which is fixed to the wings and is capable of folding forwardly beyond the wings to engage the skin of the patient to hold the cannula and the remainder of the device in position. U.S. Pat. No. 3,064,648 of Bujan discloses an anchor mounted onto an intravenous needle assembly which includes opposing wing strips of relatively flexible material formed integrally with a mounting tubing; the wing strips are pivotally connected to the mounting tubing by a section of thinner or weaker material located at the point of connection of the strips to the mounting tubing. Other U.S. patents of interest include U.S. Pat. Nos. 3,920,001; 3,906,946; 3,766,915; and, 3,769,975.

SUMMARY OF THE INVENTION

It is an object of the invention to provide a new and improved catheter assembly that provides for the transfer of medicinal fluid into the blood vessel without substantially interrupting flow of blood therethrough.

It is an object of this invention to provide a new and improved catheter assembly insertable into a blood vessel by means of a removable introducing needle, the catheter assembly providing for the transfer of medicinal fluid in either direction within the blood vessel.

It is an object of this invention to provide a new and improved catheter assembly insertable by means of a hollow, introducing needle, the catheter assembly providing a temporary bore within the blood vessel which allows for substantially uninterrupted flow of blood therethrough.

It is an object of this invention to provide an anchoring flap for the catheter assembly of the embodiments of this invention or for any other catheter which may be attached to the skin with the catheter in practically any position in order to firmly hold the catheter in position.

These objects and other objects of this invention will be described in more detail in the description of the preferred embodiment to follow. It should be understood that the objects mentioned here are exemplary only of the many objects of this invention.

These objects and other objects of this invention are provided by the catheter assembly of this invention. The catheter assembly of this invention includes an introducing needle having a point on one end thereof for insertion into a blood vessel. A hollow catheter tubular unit is slidably mounted over the introducing needle. The hollow catheter tubular unit includes a main, flexible hollow body section that terminates in an insertable end portion which is inserted into a blood vessel by means of the introducing needle. The insertable end portion includes flow means for positioning within a blood vessel for delivering medicinal fluid from the main bore of the main hollow body section into the blood vessel while allowing for substantially uninterrupted flow of blood through such vessel.

The catheter assembly of this invention is insertable into a blood vessel for providing a flow-through opening or path which allows for continued flow of the blood therethrough while at the same time delivering medicinal fluid to the blood vessel for intravenous injection.

The anchoring assembly, which may be used with the catheter assembly of this invention or with other catheters, cannulas or hollow needles used for fluid transfer, is mounted over such catheter or the like for slidable, longitudinal and circumferential movement to practically any position. The anchoring assembly further includes a flap positionable against the skin in practically any position for the catheter, cannula or other needle.

While a brief description of this invention is provided here, it should be understood that the features of this invention which will be claimed as patentable will be presented in the claims hereof.

BRIEF DESCRIPTION OF THE DRAWINGS

FIG. 3 is a schematic, isometric view of the catheter unit and anchoring assembly used to aid in holding the catheter unit stable in a blood vessel;

FIG. 4 is a schematic, sectional view illustrating the insertion of the catheter assembly of this invention into a blood vessel;

FIG. 5 is a schematic, sectional view illustrating the catheter unit in an operative position within a blood vessel;

FIG. 6 is a sectional view of the end portion of the catheter unit in position in the blood vessel;

DESCRIPTION OF THE PREFERRED EMBODIMENT

Figure 1:
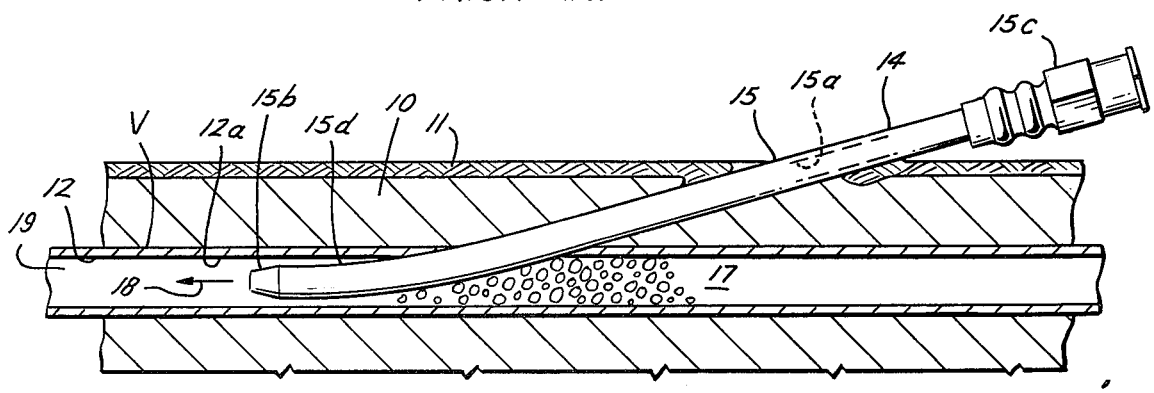
FIG. 1 is a schematic, sectional view of a type of catheter presently in widespread use, the catheter being shown inserted into a blood vessel.

FIG. 1 of the drawings illustrates a prior art catheter inserted into a blood vessel V. Throughout the figures, the cut-away skin section of FIG. 1 schematically illustrates the blood vessel V positioned in a subcutaneous layer 10 below skin 11. The blood vessel V may be either a vein or artery. The direction of blood flow through the blood vessel may either by distal (toward the extremities of the body) or proximal (toward the heart). The blood vessel V includes a bore or lumen 12 which is formed by interior vessel wall 12a.

The prior art catheter 14 of FIG. 1 includes a hollow, flexible body 15 having a bore 15a therethrough. The body 15 terminates in a tapered, open end 15b on one end and in a hub 15c at the other end. The prior art catheter is originally mounted over an introducing needle (identical to the needle N of FIG. 3) which is slidably mounted within the bore 15a. The introducing needle terminates in a sharp, exposed point used to insert the open end 15b of the catheter 14 into the blood vessel V. Thereafter, the introducing needle is removed, and the catheter hub 15c is attached to a tubing adapter which leads to a container for medicinal fluid. Although this prior art catheter has met with widespread acceptance in that it is commercially used extensively, serious problems are presented by its use.

Referring to FIG. 1, it is noted that a substantial part 15d of the catheter body is actually positioned within the lumen of the blood vessel V. It is necessary to position this rather substantial part 15d of the catheter 14 in the vessel lumen 12 in order to insure that the catheter 14 will not come out of the vessel V as a result of patient movement or movement of the equipment. The catheter 14 is subject to movement within the vessel V because it has been found difficult to anchor the catheter body 15 completely against patient and/or equipment movement. For the material of the catheter body 15 is a very smooth, friction-free synthetic material such as polytetrafluoroethylene. The reason for the use of such friction-free material is to enhance insertion of the catheter into the vessel V; however, the disadvantage is that the very smooth outside surface of the catheter body 15 also enhances movement of the inserted portion 15d within the vessel V. This effect is sometimes called "plowing" and is a source of agitation to the vessel and surrounding tissue. Further, the insertion of portion 15d of the catheter 15 into the vessel V also causes a blockage of blood flow. Depending on the size of the vessel, perhaps 80% to 90% of the cross-sectional area of the vessel may actually be blocked by the inserted catheter portion 15d. Such blockage may cause a blood clot in the upstream portion 17. Also, the elimination of blood flow may cause a bacteria buildup in the area 17 upstream or behind the inserted catheter portion 15d. The combination of undesired movement of the inserted catheter body 15 and blockage of blood flow may cause one or more of the following complications: bruising of venipuncture site; swelling of the surrounding tissue; thrombosis; phlebitis; thrombophlebitis; and possibly septicemia. These very serious complications have at least in part prompted the invention described here. Other problems include the fact that the catheter 14 only feeds in one direction 18. If any blockage or clot occurs downstream 19 of the direction of flow 18, the catheter itself will prevent the medicinal fluid from flowing in the upstream direction.

Figure 2:
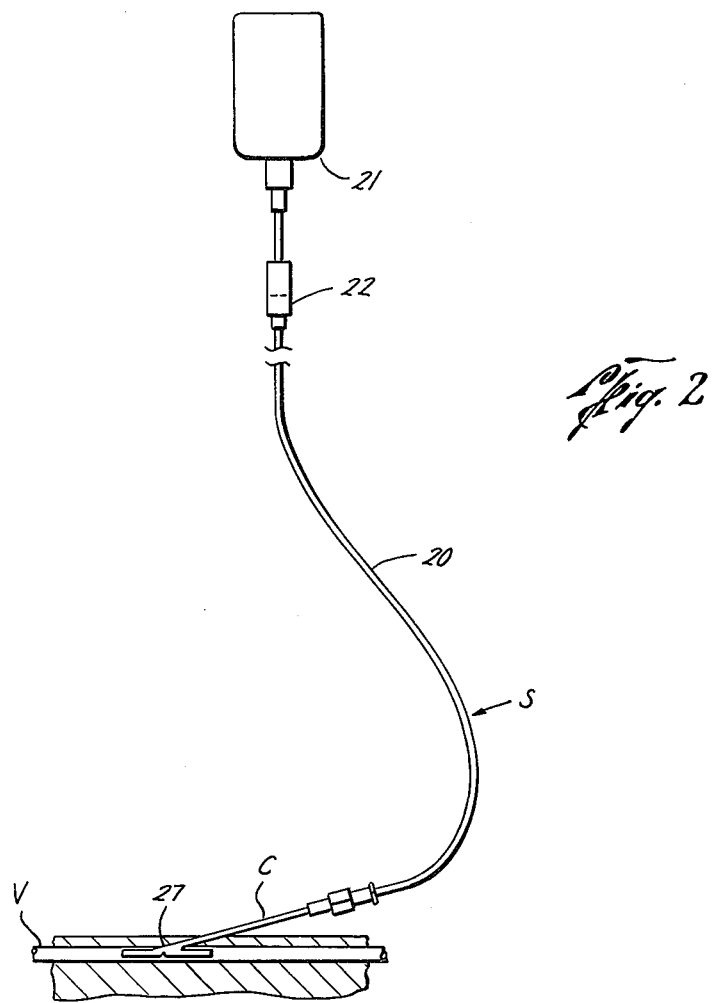
FIG. 2 is a partly schematic view of the entire catheter system of this invention illustrated in position in a blood vessel and connected to a source of fluid for intravenous injection.

The new and improved catheter system S is illustrated in FIG. 2. The catheter system S includes the insertable catheter unit C which is connected to a fluid transfer tube 20, which in turn is connected to a fluid source or container 21. A medical flow control valve of known variety 22 is generally positioned between the transfer tube 20 and the container 21 in order to meter out the medicinal fluid for transfer through the tube 20 and catheter unit C into the vessel V. The principal embodiment for the catheter unit C of this invention is illustrated in the inserted position in FIGS. 2, 3, 5 and 6. FIG. 3, a perspective view, illustrates the structural detail of the catheter most clearly. FIG. 4 shows the catheter unit C in combination with the introducing needle N, which combine to form catheter assembly A which is initially inserted into the blood vessel V.

The catheter unit C includes a main, flexible hollow body 25 which terminates on one end in a metal hub 26 and on the other end in an insertable end portion 27 which is formed integrally with the main, flexible hollow body 25. The hub 26 may be either plastic or metal and is adapted to be connected to any well-known type of adapter connected to a transfer tube such as 20. For the purposes of definition herein, the insertable end portion 27 will be defined at least approximately as that portion of the catheter unit C which actually is positioned within the lumen 12 of the blood vessel V. The flexible hollow body 25 has a bore 25a extending longitudinally therethrough, the bore 25a being defined by interior wall 25b.

The insertable end portion 27 includes flow means generally designated by the number 30 insertable into the vessel V for delivering medicinal fluid from the main body bore 25a into the blood vessel V and allowing for substantially uninterrupted flow of blood through the vessel. The flow means 30 includes bi-directional means for delivering the medicinal fluid in either direction, upstream or downstream, distally or proximally, in the blood vessel V. The flow means 30 further includes temporary bore forming means 32 for temporarily forming a bi-directional bore, generally designated by the number 33, within the blood vessel V in communication with the bore 25a of the main body 25 for allowing continuous flow of blood simultaneously with the transfer of medicinal fluid through the bore 25a into the bi-directional bore 33 and thus into the blood vessel V.

The flow means 30 and temporary bore forming means 32 of the insertable end portion 27 basically include a first end section 35 which is formed integrally with the main body 25 but extends or deviates therefrom at an obtuse angle 36, which may be measured wall to wall or at the intersection of the longitudinal axes thereof. The first end section 35 terminates in a tapered end 35a about end opening 35b. The first end section 35 is hollow and has a bore section 35c formed therein. The bore section 35c is in fluid communication with the bore 25a of the main body 25 of the catheter unit C.

The flow means 30 and temporary bore forming means 32 includes a second foldable or collapsible flow section 38 which is foldable against the main body 25 for insertion into the blood vessel V and is movable to an open or active position allowing for continued flow of blood through the vessel V while injecting medicinal into the vessel. The foldable section 38 includes a tubular or sleeve portion 39 which, in the open or active position, forms a cylindrical interior wall 39a and thus a second bore portion 40. The tubular portion 39 is slit longitudinally along line 41 between tapered end 42 and a tab portion 43 thereof. The tab portion 43 is formed by a U-shaped cut in the wall 39a.

The tubular section 39 is formed integrally with the first section 35 and the main body 25, all of which are formed of a relatively friction-free, flexible material such as polytetrafluoroethylene. A notch 44 is formed between the first and second sections 35 and 38.

The first section 35 and second section 38 of the flow means 30 and temporary bore forming means 32 are illustrated in the open, active position in FIGS. 2, 3, 5 and 6. In this active position, the first section bore 35c is aligned with the second, collapsible section bore 40 to form the continuous bore mean 33 which is basically coaxial with the blood vessel V and allows for a continuation of blood flow through the vessel. In this manner, the medicinal fluid provided through main body bore 25a from transfer tube 20 and container 21 is directed into the blood stream in the vessel V without interrupting the flow of blood.

Figure 7:
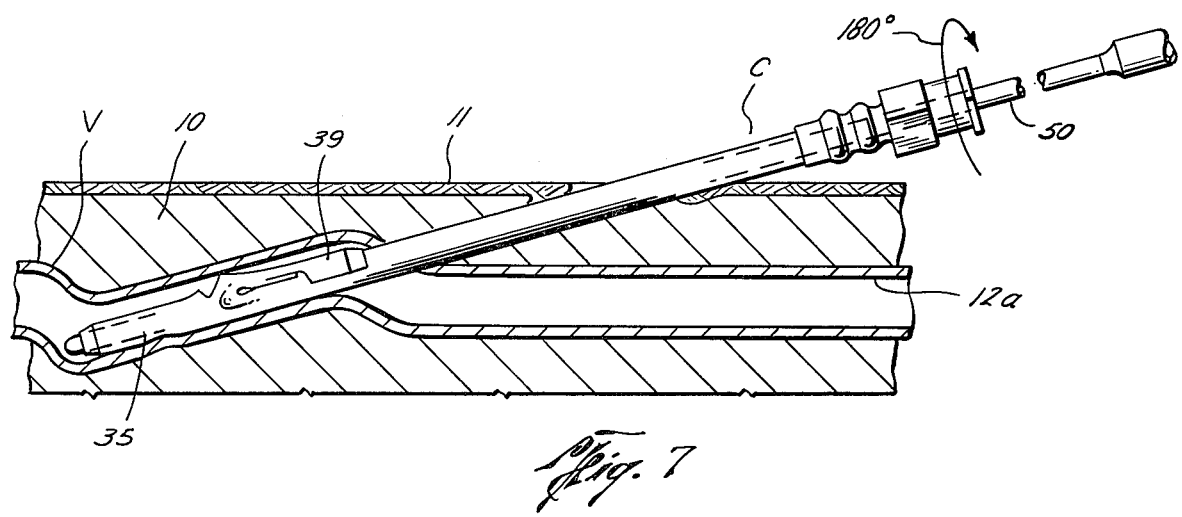
FIG. 7 is a schematic, sectional view of a blood vessel illustrating the preparation of the catheter unit for removal from the blood vessel.

The collapsed or folded position for the second sleeve or tubular portion 39 of the end portion 27 is illustrated in FIGS. 4 and 7. In FIG. 4, the complete catheter assembly A is illustrated during insertion into the blood vessel V. The second, foldable section 39 is made of a flexible material such as previously mentioned so that the section is openable along the longitudinal slit 41 for placement directly against the catheter body 25 in a substantially flat, collapsed position. In the folded or collapsed position illustrated in FIG. 4, the second or foldable section 39 fits substantially flush against the body 25 in order to present little obstruction to insertion of the complete end portion 27. In the collapsed position of FIG. 4, the notched out portion 44 reduces the amount of material of the section 39 which protrudes or would otherwise form an obstruction to insertion of the assembly A.

Introducing needle N is also illustrated in detail in FIG. 4. The introducing needle N is a hollow, metal needle or cannula which is positioned in the bore 25a of the main catheter body 25 and in the bore 35c of the first tubular section 35. The needle N extends through the first tubular section bore 35c and terminates in a protruding, sharp end 45 for penetrating the skin 11, the subcutaneous tissue 10 and the blood vessel V. The needle N is hollow in order to initially direct therethrough blood from the vessel V into a flash chamber 46. The flash chamber 46 is of any suitable construction to provide an initially closed chamber to receive blood so that the user can easily ascertain when the needle end 45 is properly positioned within a blood vessel V. When the entire end portion 27 including the collapsible sleeve section 39 is fully positioned within the vessel V, the needle N may be removed and the body 25 of the catheter unit C flexed or otherwise manipulated to push the collapsible section 39 to the open position illustrated in FIGS. 2, 3, 5 and 6.

The first and second tubular sections 35 and 39 in the open position provide substantial advantages over prior, known catheters. For example, the extended sections 35 and 39 cooperate to provide a bore 33 all the way through the end portion 27 to allow for continued, substantially unobstructed blood flow through the vessel V during injection of a medicinal fluid through the catheter body bore 25a. Should the downstream side 19 become blocked, the medicinal fluid may be fed into the upstream side of the blood stream so that fluid flow will not be completely shut off. Of course, it is understood that such fluid flow may be reduced due to the upstream pressure, but it at least eliminates a complete loss of intravenous injection of medicinal fluid. Further, the simultaneous flow of fluid through the main body bore 25a and in the first section bore 35c will be enhanced due to the continued flow of blood through the bore 40 of the open section 39. This is due to the "Venturi" effect, which is well-known in other arts. The first and second tubular sections 35 and 39 cooperate with the main body portion 25 to hold the entire catheter unit C in the blood vessel V, thus at least partly preventing the present difficulties with undesired movement of the inserted catheter 14 of FIG. 1.

The removal of the catheter unit C is illustrated in FIG. 7. In order to remove the catheter unit C, a solid, blunt-end, metal shaft or obdurator 50 is inserted into the catheter body bore 25a and through the bore 35c of the first section 35 of the flow means 30 and temporary bore forming means 32. The obdurator 50 is then rotated 180° thus causing the catheter unit C to roll over. As the catheter unit C rolls over, the collapsible section 39 is forced against the wall 12a of the blood vessel V thus opening and moving the foldable section 39 to the folded position, or at least to a position substantially adjacent to and against the body 25. The catheter unit C may then be gripped along with the obdurator 50 and the complete assembly pulled out of the blood vessel V. It is understood that digital pressure right above the collapsible section 39 may also be necessary to pressure the collapsible section 39 sufficiently to force it to collapse and fold against the body 25.

Figure 8:
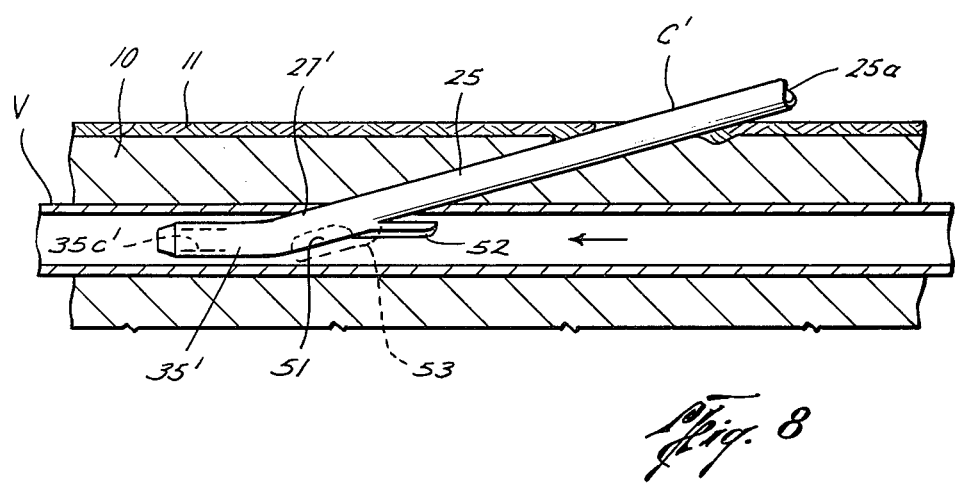
FIG. 8 is a schematic, sectional view of a blood vessel illustrating an alternate embodiment of the catheter unit.

FIG. 8 illustrates an alternate embodiment C' for the catheter unit. The same numbers and letters will identify the same parts. Again, the main body 25 has a hollow bore 25a therethrough and is joined to an insertable end section 27'. The insertable end section 27' includes a first tubular section 35' forming a bore 35c' therein. An opening 51 is formed at the rear of the insertable portion 27' and a flexibly mounted flap 52 is attached just above the opening 51. The flap 52 may again be formed integrally with the remainder of the catheter unit C'. The flap 52 is initially in a position upwardly of the opening 51 and flush against the catheter body 25. After insertion of the catheter C' and in particular end portion 27' into the vessel V by means of an introducing needle N, the body 25 for the catheter unit C' is manipulated so that the flap 52 moves downwardly to the slightly open position shown in FIG. 8. In this position, blood may continue to flow through the blood vessel V by flowing through opening 51 and through the bore 35c' of the first section 35'. In order to remove the catheter unit C', a blunt obdurator 50 is again inserted into the body bore 25a and end portion 35' and the entire assembly is rotated 180°. As the catheter unit C' and obdurator 50 are pulled outwardly of the blood vessel V, the flap 52 is moved to the closed position 53 illustrated in scored lines in FIG. 8. The flap is curved to conform to the curvature of the main body 25 and first section 35' in this position.

Returning now to FIG. 3, an anchor assembly 60 is positioned over the main catheter body 25 for attachment to the outside surface of the skin 11 for the purpose of holding the catheter body 25 in a variety of different positions in order to prevent damage to the blood vessel V or to the skin area surrounding the catheter body 25. The anchor assembly 60 includes a sleeve section 61 having a cylindrical bore 61a therethrough. The sleeve section 61 is mounted over the main body 25 of the catheter unit C for slidable movement longitudinally and circumferentially with respect to the catheter body 25. An anchoring flap section 62 of a substantially rectangular configuration is integrally attached to the sleeve section 61 by a bending section 63. The flexible attachment at 63 of the anchor flap 62 to the sleeve 61 provides even greater flexibility to the entire unit since the flap 62 may be rotated and tilted in various positions with respect to the sleeve section 61. In this manner, the sleeve section 61, bending section 63 and flap 62 cooperate to position the flap 62 flush against the skin 11 notwithstanding the catheter body 25 being in a variety of different positions. Suitable tape 64 is then placed over the flap section 62 to secure the anchor assembly 60 in place. The anchor assembly 60 may be utilized with the catheter units C or C' of this invention and further may be utilized with the standard catheters, cannulas or needles such as described in the prior patents mentioned or in FIG. 1.

The foregoing disclosure and description of the invention are illustrative and explanatory thereof, and various changes in the size, shape and materials as well as in the details of the illustrated construction may be made without departing from the spirit of the invention.

I claim:

1. A catheter assembly for insertion into a blood vessel for intravenous injection of medicinal fluid, comprising:
   an introducing needle having a point on a first end thereof for insertion into a blood vessel;
   a hollow catheter tubular unit slidably mounted over said introducing needle for insertion into such blood vessel with said introducing needle, said hollow catheter tubular unit including a main, flexible hollow body section having a main bore therethrough, said main, hollow body section terminating in an insertable end portion at one end for insertion into said blood vessel and in a connector at the other end thereof for connection to an intravenous fluid supply after removal of said introducing needle;
   said insertable end portion including flow means insertable into said blood vessel for delivering medicinal fluid from said main bore into such blood vessel while allowing for substantially uninterrupted flow of blood through such blood vessel, said insertable flow means including:
   said end portion including a first end section having an end in fluid communication with said bore of said main body section and terminating in a first opening at the end thereof and having a second opening spaced from the first opening; and
   a foldable flow section being movable between a folded position in which said end portion with said foldable flow section is inserted into such blood vessel and an open position in such blood vessel in which said flow section allows blood and intravenous fluid flow through said second opening and said first opening.

2. The structure set forth in claim 1, wherein:
said end portion has an axis which is at an obtuse angle with respect to the longitudinal axis of said main body portion.

3. The structure set forth in claim 1, including:
said foldable flow section being a flap flexibly attached to said main body for movement between a position adjacent to said body in a folded position during insertion and being movable to an open position in such blood vessel to allow for flow of blood through said second opening, and first section bore and said first section opening.

4. The structure set forth in claim 1, wherein said foldable flow section includes:
a sleeve section formed with said end portion, said section having a bore therethrough, which sleeve section bore is in fluid communication with said first section and main hollow body section bores through said second opening; and
said sleeve section being movable between a folded position in which said sleeve section is positioned substantially adjacent to said body and an open position in such blood vessel in which said sleeve section is positioned in such blood vessel to allow flow therethrough.

5. The structure set forth in claim 4, including:
said sleeve section is split longitudinally thereof and is flexibly attached to said end portion for fitting over said end portion in said foldable position such that said end portion with said sleeve section in said folded position is easily inserted into the skin into a blood vessel.

6. The structure set forth in claim 5, including:
said first section and foldable flow section being joined together to form a substantially continuous flow bore with said foldable section in an open position in order to allow for uninterrupted flow of blood through such vessel.

7. The structure set forth in claim 4, including:
said sleeve section bore being substantially alignable with said first section openings.

8. The structure set forth in claim 4, including:
said foldable flow section being flexibly connected to said first section and main body for movement from said open position to said folded position prior to removal from such blood vessel.

9. The structure set forth in claim 8, including:
said flap being returnable to a folded position over said second opening prior to removal of said end portion from such blood vessel.

* * * * *